United States Patent
Miyagawa et al.

(10) Patent No.: US 12,173,022 B2
(45) Date of Patent: Dec. 24, 2024

(54) METHOD FOR PRODUCING RNA

(71) Applicant: SUMITOMO CHEMICAL COMPANY, LIMITED, Chuo-ku (JP)

(72) Inventors: Takuya Miyagawa, Osaka (JP); Nobuaki Waizumi, Osaka (JP)

(73) Assignee: SUMITOMO CHEMICAL COMPANY, LIMITED, Chuo-ku (JP)

( * ) Notice: Subject to any disclaimer, the term of this patent is extended or adjusted under 35 U.S.C. 154(b) by 657 days.

(21) Appl. No.: 17/599,409

(22) PCT Filed: Feb. 28, 2020

(86) PCT No.: PCT/JP2020/008313
§ 371 (c)(1),
(2) Date: Sep. 28, 2021

(87) PCT Pub. No.: WO2020/202949
PCT Pub. Date: Oct. 8, 2020

(65) Prior Publication Data
US 2022/0213134 A1  Jul. 7, 2022

(30) Foreign Application Priority Data
Mar. 29, 2019 (JP) ................................. 2019-067993

(51) Int. Cl.
*C07H 1/00* (2006.01)
*C07H 21/02* (2006.01)

(52) U.S. Cl.
CPC ............... *C07H 1/00* (2013.01); *C07H 21/02* (2013.01)

(58) Field of Classification Search
None
See application file for complete search history.

(56) References Cited

U.S. PATENT DOCUMENTS

| | | | |
|---|---|---|---|
| 6,995,259 B1 | 2/2006 | Vargeese et al. | |
| 7,205,399 B1 | 4/2007 | Vargeese et al. | |
| 7,777,023 B2 | 8/2010 | Vargeese et al. | |
| 9,359,396 B2 * | 6/2016 | Chaix | B05D 7/00 |
| 2004/0127357 A1 | 7/2004 | Simpson et al. | |
| 2009/0005536 A1 | 1/2009 | Rothstein et al. | |
| 2011/0092690 A1 | 4/2011 | Hayakawa et al. | |
| 2014/0235435 A1 | 8/2014 | Miyahara et al. | |
| 2019/0076814 A1 * | 3/2019 | Dabrowski | C12N 15/1093 |

FOREIGN PATENT DOCUMENTS

| | | |
|---|---|---|
| CN | 108176387 A | 6/2018 |
| EP | 2 772 466 A1 | 9/2014 |
| JP | 2958338 B | 10/1999 |
| JP | 2006-502856 A | 1/2006 |
| JP | 2011-88843 A | 5/2011 |
| WO | WO 2004/035170 A2 | 4/2004 |
| WO | WO 2013/062105 A1 | 5/2013 |
| WO | WO 2017/0119503 A1 | 7/2017 |
| WO | WO-2017119503 A1 * | 7/2017 ............. C12M 1/00 |

OTHER PUBLICATIONS

WO2017119503a1, machine translation, 2017. (Year: 2017).*
Guzaev, Curr. Protoc. Nucleic Acid Chem. 53:3.1.1-3.1.60, 2013. (Year: 2013).*
Extended European Search Report issued Jan. 4, 2023, in corresponding European Patent Application No. 20784734.4 citing documents 24-26 therein, 12 pages.
Pitsch Stefan et al., "Reliable Chemical Synthesis of Oligoribonucleotides (RNA) with 2'-O-[(Triisopropylsilyl)oxy]methyl(2'-O-tom)-Protected Phosphoramidites", Helvetica Chimica Acta, vol. 84, No. 12, Dec. 1, 2001, pp. 3773-3795, XP093009841.
Richard T. Pon: "Solid-Phase Supports for Oligonucleotide Synthesis" In: "Current Protocols in Nucleic Acid Chemistry", Jan. 1, 2001, John Wiley & Sons, Inc., Hoboken, NJ, USA, XP055001056.
Damha M. J. et al., "An Improved Procedure For Derivatization Of Controlled-Pore Glass Beads For Solid-Phase Oligonucleotide Synthesis", Nucleic Acids Research, Oxford University Press, GB, vol. 18, No. 13, Jul. 11, 1990, pp. 3813-3821, XP000562627.
International Search Report issued May 26, 2020 in PCT/JP2020/008313 (submitting English translation only), 3 pages.
International Preliminary Report on Patentability and Written Opinion of the International Searching Authority issued Sep. 28, 2021 in PCT/JP2020/008313 (submitting English translation only), 6 pages.
International Search Report issued May 19, 2020 in PCT/JP2020/008318 (submitting English translation only), 2 pages.
International Preliminary Report on Patentability and Written Opinion of the International Searching Authority issued Sep. 28, 2021 in PCT/JP2020/008318 (submitting English translation only), 7 pages.
International Search Report issued May 19, 2020 in PCT/JP2020/008321 (submitting English translation only), 2 pages.

(Continued)

*Primary Examiner* — Layla D Berry
(74) *Attorney, Agent, or Firm* — Oblon, McClelland, Maier & Neustadt, L.L.P.

(57) ABSTRACT

The present invention provides a method for preparing RNA by a phosphoramidite solid-phase synthesis using an porous inorganic carrier containing a primary amino group, the method being able to bring about an increased purity even in the synthesis of medium-stranded to long-stranded RNA. In the method for producing RNA, an amount of the primary amino group contained in the porous inorganic carrier satisfies the following formula (1): $0.7 \leq (I \times R)/S \leq 1.8$ [wherein, I is an amount of the amino group per unit mass of the porous inorganic carrier (µmol/g), as measured by a 2-nitrobenzenesulfonic acid adsorption method; R is a ratio of the primary amino group in the total amino groups contained in the porous inorganic carrier (amount of primary amino group/amount of total amino groups); and S is a specific surface area ($m^2/g$) of the porous inorganic carrier as measured by a nitrogen adsorption method].

10 Claims, No Drawings
Specification includes a Sequence Listing.

(56) References Cited

OTHER PUBLICATIONS

International Preliminary Report on Patentability and Written Opinion of the International Searching Authority issued Sep. 28, 2021 in PCT/JP2020/008321 (submitting English translation only), 7 pages.
International Search Report issued May 19, 2020 in PCT/JP2020/008323 (submitting English translation only), 2 pages.
International Preliminary Report on Patentability and Written Opinion of the International Searching Authority issued Sep. 28, 2021 in PCT/JP2020/008323 (submitting English translation only), 6 pages.
International Search Report issued May 19, 2020 in PCT/JP2020/008325 (submitting English translation only), 2 pages.
International Preliminary Report on Patentability and Written Opinion of the International Searching Authority issued Sep. 28, 2021 in PCT/JP2020/008325 (submitting English translation only), 6 pages.
J. Katzhendler, et al. "The Effect of Spacer, Linkage and Solid Support on the Synthesis of Oligonucleotides" Tetrahedron, vol. 45, No. 9, 1989, pp. 2777-2792.
Kiyohisa Imada, et al., "Studies on the Internal Surface of Porous Glass and Chemical Modification thereof" Journal of the Chemical Society of Japan, vol. 4, 1990, pp. 407-414 (with English translation).
Glenn Tong, et al., The Synthesis of Oligonucleotide-Polyamide Conjugate Molecules Suitable as PCR Primers, Journal of Organic Chemistry, vol. 58, No. 8, 1993, pp. 2223-2231.
J-Y. Wang, et al., "Preparation of a New Support for Solid Phase Synthesis of Glass Bead Surface with Amino" Hecheng Huaxue, Chinese Journal of Synthetic Chemistry, vol. 21, No. 1, 2013, pp. 66-69 (with English Abstract).
Roxana S. Timofte, et al., "Preparation of Silane-Grafted Pellets: Silica Bound Reagents in a Very Convenient Form" Tetrahedron Letters, vol. 45, 2004, pp. 39-42.
U.S. Appl. No. 17/599,297, filed Sep. 28, 2021, Kanako Yamazaki, et al.
U.S. Appl. No. 17/599,787, filed Sep. 29, 2021, Masaki Kitahara, et al.
U.S. Appl. No. 17/599,700, filed Sep. 29, 2021, Takashi Arimura, et al.
U.S. Appl. No. 17/599,249, filed Sep. 28, 2021, Syusaku Hara, et al.

\* cited by examiner

SEQUENCE LISTING

<160> NUMBER OF SEQ ID NOS: 3

<210> SEQ ID NO 1
<211> LENGTH: 24

```
<212> TYPE: RNA
<213> ORGANISM: Artificial Sequence
<220> FEATURE:
<223> OTHER INFORMATION: Synthesized RNA

<400> SEQUENCE: 1
agcagaguac acacagcaua uacc                                          24

<210> SEQ ID NO 2
<211> LENGTH: 26
<212> TYPE: RNA
<213> ORGANISM: Artificial Sequence
<220> FEATURE:
<223> OTHER INFORMATION: Synthesized RNA

<400> SEQUENCE: 2
gguauaugcu guguguacuc ugcuuc                                        26

<210> SEQ ID NO 3
<211> LENGTH: 103
<212> TYPE: RNA
<213> ORGANISM: Artificial Sequence
<220> FEATURE:
<223> OTHER INFORMATION: Synthesized RNA

<400> SEQUENCE: 3
auaacucaau uuguaaaaaa guuuuagagc uagaaauagc aaguuaaaau aaggcuaguc    60
cguuaucaac uugaaaaagu ggcaccgagu cggugcuuuu uuu                    103
```

METHOD FOR PRODUCING RNA

CROSS-REFERENCE TO RELATED APPLICATIONS

The present application is a 35 U.S.C. § 371 national stage patent application of International patent application PCT/JP2020/008313, filed on Feb. 28, 2020, which is based on and claims the benefits of priority to Japanese Application No. 2019-067993, filed on Mar. 29, 2019. The entire contents of these applications are incorporated herein by reference.

TECHNICAL FIELD

This application claims priority to and the benefit of Japanese Patent Application No. 2019-067993 filed on Mar. 29, 2019, the entire contents of which are incorporated herein by reference.

The present invention relates to a method for preparing RNA.

BACKGROUND ART

As a chemical synthesis method of a nucleic acid, a solid-phase synthesis method by a phosphoramidite method has been widely used. In this method, first, a functional group such as an amino group is introduced onto a solid-phase carrier using a silane coupling agent or the like, and a nucleoside providing a 3'end of the nucleic acid is bound to the functional group. Then, a nucleic acid elongation reaction is carried out on the solid-phase carrier starting from the nucleoside.

In the solid-phase synthesis method, when a strand length of the nucleic acid to be synthesized becomes long, a synthesis efficiency drastically decreases, and consequently, a large amount of by-products is prone to be produced and mixed. It is considered that this is because the nucleic acid molecules that elongates on the surface of the solid-phase carrier interfere with each other, resulting in inhibition of elongation reaction, occurrence of side reactions, or the like.

In order to prevent interference between nucleic acid molecules on the surface of the solid-phase carrier, it is conceivable to reduce the amount of functional group to be introduced on the solid-phase carrier. For example, Patent Document 1 describes that a synthesis yield of 15-mer DNA was improved by using a solid-phase carrier into which an alkylamino group was introduced at a ratio of 0.3 to 2.5 $\mu mol/m^2$ as a quantitative value with picric acid.

CITATION LIST

Patent Document

Patent Document 1: JP 2958338 B2

SUMMARY OF THE INVENTION

Problems To Be Solved by Invention

It is considered that if an amount of amino group supported on the solid-phase carrier is reduced, the interference between the nucleic acid molecules could be prevented to allow an improved synthesis yield and a reduced by-products amount. However, if the amount of amino group supported on the solid-phase carrier is too low, the productivity of nucleic acid would decrease. Therefore, in order to improve the yield and purity of nucleic acid while maintaining the productivity of the nucleic acid, the amount of amino group supported on the solid-phase carrier should be within an appropriate range.

Further, in general, RNA synthesis is more difficult than DNA synthesis. In particular, in the synthesis of long stranded RNA, it is required to control the amount of amino group supported on the solid-phase carrier within an optimum range.

The present invention has been made in view of the above situation, and the problem to be solved by the present invention is to provide a method for preparing RNA, which can improve the purity even in medium-stranded to long-stranded RNA synthesis.

Means to Solve Problems

A method for preparing RNA according to one aspect of the present invention is a method for preparing RNA by a phosphoramidite solid-phase synthesis method using an inorganic porous carrier containing a primary amino group, wherein an amount of the primary amino group contained in the inorganic porous carrier satisfies the following formula (1):

(hereinafter, referred to as "Preparation method of the present invention" or "Present preparation method")

$$0.7 \leq (I \times R)/S \leq 1.8 \tag{1}$$

wherein,

I: an amount of amino group per unit mass of the inorganic porous carrier ($\mu mol/g$), which is measured by a 2-nitrobenzenesulfonic acid adsorption method;

R: a ratio of primary amino group to total amino groups contained in the inorganic porous carrier (amount of the primary amino group/amount of the total amino groups);

S: a specific surface area of the inorganic porous carrier ($m^2/g$), which is measured by a nitrogen adsorption method.

In the method for preparing RNA according to one aspect of the present invention, the amount of the primary amino group contained in the inorganic porous carrier satisfies the following formula (1'):

$$1.3 \leq (I \times R)/S \leq 1.8 \tag{1'}$$

wherein,

I: an amount of amino group per unit mass of the inorganic porous carrier ($\mu mol/g$), which is measured by the 2-nitrobenzenesulfonic acid adsorption method;

R: a ratio of primary amino group to total amino groups contained in the inorganic porous carrier (amount of the primary amino group/amount of the total amino groups);

S: a specific surface area of the inorganic porous carrier ($m^2/g$), which is measured by the nitrogen adsorption method.

The method for preparing RNA according to one aspect of the present invention may be a method wherein an inorganic porous substance in the inorganic porous carrier is porous glass.

The method for preparing RNA according to one aspect of the present invention may be a method wherein a pore size (mode diameter) of the inorganic porous carrier is within a range of 90 to 120 nm.

The method for preparing RNA according to one aspect of the present invention may be a method wherein a pore size (mode diameter) of the inorganic porous carrier is within a range of 120 to 200 nm.

The method for preparing RNA according to one aspect of the present invention may be a method which comprises steps 1 to 4 as follows:

step 1) a step of reacting the inorganic porous carrier containing the primary amino group with a linker containing a nucleoside having a protected hydroxyl group to introduce the nucleoside having the protected hydroxyl group into the inorganic porous carrier;

step 2) a step of filling a column of a nucleic acid solid-phase synthesizer with the inorganic porous carrier into which the nucleoside is introduced;

step 3) a step of repeating a cycle including deprotection, coupling with an amidite compound, and oxidation multiple times by means of the nucleic acid solid-phase synthesizer; and step 4) a step of cleaving RNA having the protected hydroxyl group from the inorganic porous carrier after the step 3, and then deprotecting.

The method for preparing RNA according to one aspect of the present invention may be a method wherein the linker is a succinyl linker.

The method for preparing RNA according to one aspect of the present invention may be a method wherein the cycle described in the above step 3) is repeated 40 times or more.

EFFECT OF INVENTION

The present invention provides a method for preparing RNA which can improve the purity even in medium-stranded to long-stranded RNA synthesis.

MODE FOR CARRYING OUT THE INVENTION

As used herein, when a certain numerical range is referred to as "A to B" or "A-B", it means a range represented by "from A or more to B or less" unless otherwise stated.

The method for preparing RNA according to one aspect of the present invention is a method for preparing RNA by a phosphoramidite solid-phase synthesis method using an inorganic porous carrier containing a primary amino group, wherein an amount of the primary amino group contained in the inorganic porous carrier satisfies the following formula (1):

$$0.7 \leq (I \times R)/S \leq 1.8 \qquad (1')$$

wherein,

I: an amount of amino group per unit mass of the inorganic porous carrier (μmol/g), which is measured by a 2-nitrobenzenesulfonic acid adsorption method;

R: a ratio of primary amino group to total amino groups contained in the inorganic porous carrier (amount of the primary amino group/amount of the total amino groups);

S: a specific surface area of the inorganic porous carrier ($m^2/g$), which is measured by a nitrogen adsorption method.

Inorganic Porous Carrier

The inorganic porous carrier to be used in the preparation method of the present embodiment is an inorganic porous carrier into which a primary amino group is introduced, wherein the amount of the primary amino group satisfies the above formula (1).

The inorganic porous carrier is, for example, a carrier in which the primary amino group is covalently bound to the surface of the inorganic porous substance through any kind of chemical bond, and examples thereof include an inorganic porous carrier obtained by reacting an inorganic porous substance having a silano group on its surface with a silane coupling agent having an amino group (or a protected amino group).

Inorganic Porous Substance

The inorganic porous substance is not particularly limited, and a substance to be generally used as a substrate for a carrier for solid-phase nucleic acid synthesis can be used for the inorganic porous substance. In particular, the inorganic porous substance is preferably silica gel, zeolite, or porous glass, and more preferably porous glass.

Examples of the porous glass include a porous glass which is commercially available under the name of CPG (Controlled Pore Glass) or the like.

A shape of the inorganic porous substance is not particularly limited, and may be any shape such as a nearly spherical shape, a polyhedral shape, a nearly pillared shape, and a crushed shape, but the shape is preferably the crushed shape from the viewpoint of filling efficiency into a column.

A particle size of the inorganic porous substance is not particularly limited, but an average particle size thereof which is measured by laser diffraction (scattering type) is within a range of 1 to 1000 μm, preferably 5 to 500 μm, and more preferably 10 to 200 μm, from the viewpoint of filling efficiency into a column, liquid feeding rate in a column filling, and the like.

A pore size of the inorganic porous substance is not particularly limited, and can be appropriately selected depending on a strand length of RNA to be synthesized. Generally, when a strand length of RNA to be synthesized is long, it is preferable to select the inorganic porous substance having a large pore size. For example, when RNA of 40-mer or more is synthesized, the pore size may be 50 nm or more. For example, when RNA of 40-mer to 200-mer is synthesized, the pore size may be within a range of 50 to 300 nm. For example, when RNA of 50-mer to 200-mer is synthesized, the pore size may be within a range of 70 to 300 nm. For example, when RNA of 100-mer to 200-mer is synthesized, the pore size may be within a range of 100 to 300 nm. The pore size as described above is measured by a mercury intrusion method.

The pore size (mode diameter) is determined based on a value of X-axis at a peak top in the pore size distribution obtained by the mercury intrusion method (a graph in which the X-axis is a value of the pore size and the Y-axis is a value obtained by calculating differentially the pore volume by the pore size).

In a preferred embodiment, the pore size (mode diameter) of the inorganic porous substance may be within a range of 90 to 120 nm. In another preferred embodiment, the pore size (mode diameter) of the inorganic porous substance may be within a range of 120 to 200 nm.

The specific surface area of the inorganic porous substance is not particularly limited. Generally, as the specific surface area becomes larger, the pore size has a tendency to be smaller. The specific surface area may be generally within a range of 10 to 100 $m^2/g$. For example, when RNA of 40-mer or more (for example, 40-mer to 200-mer) is synthesized, the specific surface area is preferably within a range of 10 to 40 $m^2/g$, and more preferably 20 to 40 $m^2/g$. The specific surface area of the inorganic porous substance according to the present invention is measured by the nitrogen adsorption method. A measurement of the specific surface area according to the nitrogen adsorption method can be carried out specifically as follows.

Measurement of Specific Surface Area According To Nitrogen Adsorption Method

The measurement of the specific surface area of the inorganic porous substance as described in the examples herein by the nitrogen adsorption method was carried out according to the following procedure. The specific surface area of the inorganic porous carrier preferably has a value determined according to the following procedure within the range as described above.

For a pretreatment of sample, vacuum degassing at 120° C. for 3 hours is carried out by using a vacuum heating pretreatment device (for example, BELPREP-vacII (produced by MicrotracBell Corp.)). To 0.3 g of the pretreated sample, nitrogen gas is adsorbed at a temperature of 77 K while vacuum degassing by using a pore distribution measuring device (for example, BELSORP-mini (produced by MicrotracBell Corp.)), and then desorbed to prepare an adsorption isotherm. The specific surface area is calculated according to the BET method based on the obtained adsorption isotherm.

Amount of Primary Amino Group Contained in Inorganic Porous Carrier

The inorganic porous carrier is a carrier in which the primary amino group is introduced into the inorganic porous substance, and it contains the primary amino group. In the preparation method of the present embodiment, the amount of the primary amino group contained in the inorganic porous carrier satisfies the following formula (1):

$$0.7 \leq (I \times R)/S \leq 1.8 \quad (1')$$

wherein,

I: an amount of amino group per unit mass of the inorganic porous carrier ($\mu$mol/g), which is measured by a 2-nitrobenzenesulfonic acid adsorption method;

R: a ratio of primary amino group to total amino groups contained in the inorganic porous carrier (amount of the primary amino group/amount of the total amino groups);

S: a specific surface area of the inorganic porous carrier ($m^2/g$), which is measured by a nitrogen adsorption method.

The amount of the primary amino group contained in the inorganic porous carrier preferably satisfies the following formula (1'):

$$1.3 \leq (I \times R)/S \leq 1.8 \quad (1')$$

Amount of Amino Group: I

In the above formulae (1) and (1'), "I" represents an amount of amino group per unit mass of the solid-phase carrier ($\mu$mol/g), which is measured by an amount of amino group per unit mass of the inorganic porous carrier, which is measured by a 2-nitrobenzenesulfonic acid adsorption method. The "2-nitrobenzenesulfonic acid adsorption method" refers to a method for quantifying an amount of amino group based on an amount of 2-nitrobenzenesulfonic acid ionically bound to the amino group.

The measurement of the amount of amino group according to the 2-nitrobenzenesulfonic acid adsorption method can be carried out as follows.

About 30 mg of the inorganic porous carrier is placed in a Pasteur pipette or the like which is sealed with absorbent cotton, and washed by passing a solution 1 mL of N,N-diisopropylethylamine (DIPEA) in tetrahydrofuran (THF) (DIPEA 5% by volume) through the inorganic porous carrier. Then, a solution 1 mL of 2-nitrobenzenesulfonic acid in THF (2-nitrobenzenesulfonic acid 50 mM) is passed through the inorganic porous carrier four times, and then 1 mL of THF is passed four times for washing. Then, using a container such as a 10 mL measuring flask as a receiver, a mixed solution, in which a diluted aqueous ammonia solution (a solution in which 28% ammonia aqueous solution and water are mixed at a volume ratio of 1:100) and acetonitrile are mixed at a volume ratio of 1:1, is passed through the inorganic porous carrier. An aqueous solution of acetonitrile (acetonitrile 15% by volume) is added to the eluted solution received in the receiver to prepare 10 mL of the solution, and the solution is analyzed by high performance liquid chromatography (HPLC) to measure the peak area value of 2-nitrobenzenesulfonic acid. The HPLC analysis conditions are not particularly limited as long as the 2-nitrobenzenesulfonic acid can be measured, and examples thereof include, for example, the analysis conditions shown in Examples described later.

When the above peak area value of 2-nitrobenzenesulfonic acid is referred to as "B", a mass of the inorganic porous carrier used in the analysis is referred to as "M", a slope of a calibration line prepared by using the standard solution of 2-nitrobenzenesulfonic acid is referred to as "a", and an intercept of the calibration line is referred to as "b", the amount of amino group can be calculated as follows. In the following formula, "203.17" is a molecular weight of 2-nitrobenzenesulfonic anhydride ($C_6H_5NO_5S$).

$$\text{Amino group amount } I = (B-b)/(203.17 \text{ Ma}) \times 10$$

Creation of Calibration Line

The calibration line of 2-nitrobenzenesulfonic acid can be created as follows.

First, a content of 2-nitrobenzenesulfonic acid is determined by neutralization titration (because a commercial product is a hydrate thereof). Then, at least three kinds of 2-nitrobenzenesulfonic acid solutions having different concentrations are prepared, and are subjected to HPLC analysis. The area value of the peak in the HPLC analysis is set to a vertical axis, and the concentration of 2-nitrobenzenesulfonic acid is set to a horizontal axis, and the results of HPLC are plotted, and a linear approximation is performed to obtain the calibration line.

In the inorganic porous carrier to be used in the preparation method of the present embodiment, the amount of amino group is not particularly limited as long as the effect of the preparation method of the present embodiment is not impaired, and the amount of amino group can be appropriately selected depending on the strand length of RNA to be synthesized. In general, it is preferable that the amino group amount I is lower as the strand length of the RNA to be synthesized becomes longer. For example, when RNA of 40-mer or more (for example, 40-mer to 200-mer) is synthesized, the amino group amount I may be within a range of 20 to 110 $\mu$mol/g. For example, when RNA of 100-mer or more (for example, 100-mer to 200-mer) is synthesized, the amino group amount I may be within a range of 20 to 60 $\mu$mol/g.

Ratio of Primary Amino Group: R

In the above formula (1), "R" represents the ratio of primary amino group to total amino groups contained in the inorganic porous carrier. For example, when an amount by mol of total amino groups contained in the inorganic porous carrier is referred to as A1, and an amount by mol of primary amino group is referred to as A2, and R can be determined based on the formula: R=A2/A1.

For example, in the case of an inorganic porous carrier supporting a Lcaa(C9) linker represented by any one of the following formulae (Lcaa(c9)-SP1) to (Lcaa(c9)-SP6), the total number of amino groups in the Lcaa(C9) linker is 2(two), and the number of primary amino group is 1(one), resulting in R=1/2.

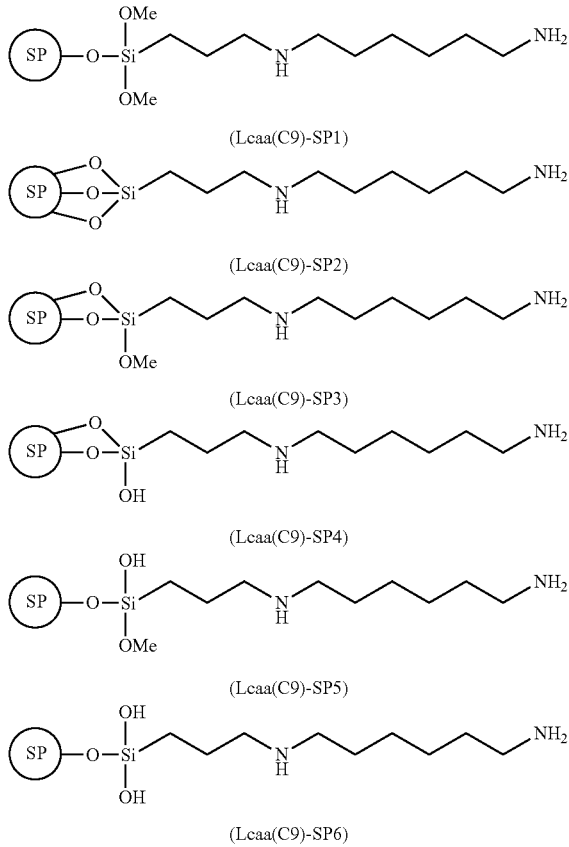

(Lcaa(C9)-SP1)

(Lcaa(C9)-SP2)

(Lcaa(C9)-SP3)

(Lcaa(C9)-SP4)

(Lcaa(C9)-SP5)

(Lcaa(C9)-SP6)

[wherein, SP represents an inorganic porous substance, and Me represents a methyl group.]

Also, for example, in the case of an inorganic porous carrier supporting an Aminopropyl linker represented by any one of the following formulae (Aminopropyl-SP1) to (Aminopropyl-SP6), the total number of amino groups in the Aminopropyl linker is 1(one), and the number of primary amino group is 1(one), resulting in R=1/1.

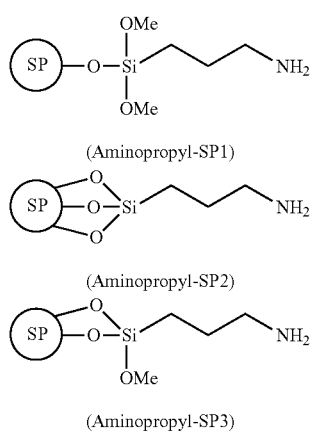

(Aminopropyl-SP1)

(Aminopropyl-SP2)

(Aminopropyl-SP3)

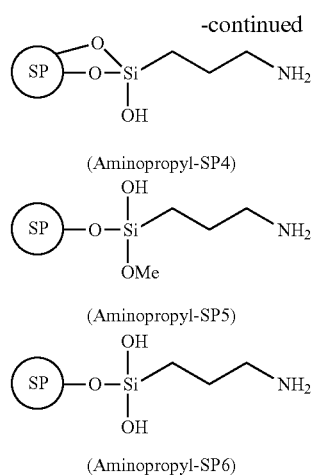

(Aminopropyl-SP4)

(Aminopropyl-SP5)

(Aminopropyl-SP6)

[wherein, SP and Me have the same meanings as described above.]

Specific Surface Area of Inorganic Porous Carrier: S

In the above formulae (1) and (1'), "S" represents the specific surface area ($m^2/g$) of the inorganic porous carrier, which is measured by the nitrogen adsorption method. The specific surface area S can be measured in the same manner as the method described in the above "[Measurement of specific surface area according to nitrogen adsorption method]".

Method for Preparing Inorganic Porous Carrier

The inorganic porous carrier to be used in the preparation method of the present embodiment can be prepared, for example, by reacting an inorganic porous substance with a silane coupling agent containing a primary amino group or a protected primary amino group. Hereinafter, the method for preparing the inorganic porous carrier by reacting the inorganic porous substance with the silane coupling agent containing the primary amino group or the protected primary amino group is described below.

The silane coupling agent is not particularly limited, and examples thereof include a silane coupling agent represented by the following formula (s1):

$$(R^1O)_3Si-(CH_2)_m-L-(CH_2)_nNH_2 \quad (s1)$$

[wherein, $R^1$ represents an alkyl group containing 1 to 4 carbon atoms; m represents an integer of 1 to 4; n represents an integer of 2 to 8; and L represents a single bond or —NH—].

Specifically, examples of the silane coupling agent include an aminoalkylalkoxysilane containing one primary amino group such as aminopropyltrimethoxysilane, aminopropyltriethoxysilane, and aminoethyltrimethoxysilane; and an aminoalkylalkoxysilane containing one primary amino group and one secondary amino group such as N-2-(aminoethyl)-3-aminopropylmethyldimethoxysilane, N-2-(aminoethyl)-3-aminopropyltrimethoxysilane, [3-(6-aminohexylamino)propyl]trimethoxysilane (Lcaa(C9)), but are not limited thereto.

The reaction of the inorganic porous substance with the silane coupling agent containing the primary amino group is usually carried out in a dry organic solvent such as acetonitrile, toluene, xylene, anisole, 2-heptanone, propyleneglycol monomethyl ether acetate, N,N-dimethylformamide, or two or more thereof. In order to remove water that prevents the above reaction with the silane coupling agent, it is preferable to remove water contained in the inorganic porous substance in advance. The inorganic porous substance may be dispersed in an organic solvent such as toluene or xylene, followed by dehydration treatment, to remove the water. When dehydration treatment of the inorganic porous substance is carried out in the organic solvent, the silane coupling agent can be added to the mixture after the dehydration treatment, and the reaction of the inorganic porous substance with the silane coupling agent can be subsequently carried out.

The reaction temperature in the above reaction of the inorganic porous substance with the silane coupling agent is, for example, within a range of 0 to 110° C., and preferably 100 to 110° C., but the reaction may be carried out at a temperature near the boiling point of the organic solvent to be used, that is, the reflux temperature, depending on the silane coupling agent and the inorganic porous substance to be used. Further, the reaction time is usually within a range of about 2 to 6 hours, but the reaction time may be appropriately shortened or extended depending on the inorganic porous substance and the silane coupling agent to be used.

The amount of the silane coupling agent to be used can be appropriately set taking the specific surface area of the inorganic porous substance and the target amount of the primary amino group into a consideration.

The inorganic porous carrier obtained by the above reaction can be separated, washed, and dried by a conventional method, and used as a solid-phase carrier for RNA synthesis.

Further, after the reaction of the inorganic porous substance with the silane coupling agent, an amine compound may be further reacted with the resulting reactant product to elongate the linker. For example, when m is 1, n is 2, and L represents a single bond in the above formula (s1), the silane coupling agent represented by the formula (s1) may be reacted with the inorganic porous substance to obtain the inorganic porous carrier containing the primary amino group, and then the terminal primary amino group may be further reacted with p-nitrophenylformyl chloride to introduce a reactive carbonyl group, and various kinds of alkanediamines can be reacted with the resulting reactant product to prepare an inorganic porous carrier containing the following linker (L-1) or (L-2).

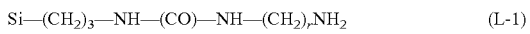

Si—(CH$_2$)$_3$—NH—(CO)—NH—(CH$_2$)$_r$NH$_2$    (L-1)

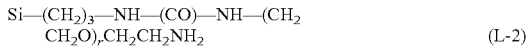

Si—(CH$_2$)$_3$—NH—(CO)—NH—(CH$_2$
CH$_2$O)$_r$CH$_2$CH$_2$NH$_2$    (L-2)

[wherein, in the formulae (L-1) and (L-2), r is an integer of 1 to 3.]

In the inorganic porous carrier prepared as described above, the amount of amino group can be calculated by the method as described above, and it may be confirmed that the amount of primary amino group satisfies the above formula (1) After that, RNA solid-phase synthesis is carried out using the inorganic porous carrier which is confirmed to satisfy the above formula (1).

Further, a solid-phase carrier in which a nucleoside is bound to the above inorganic porous carrier through a succinyl group can be synthesized, and used for the solid-phase synthesis of RNA.

RNA Synthesis

In the preparation method of the present embodiment, the solid-phase synthesis of RNA is carried out by the phosphoramidite method using the inorganic porous carrier as described above. The phosphoramidite method can be carried out by a publicly known method. Specific examples of RNA synthesis by the phosphoramidite method are shown below.

The inorganic porous carrier containing the primary amino group can be reacted with a linker containing a nucleoside in which a hydroxyl group is protected to prepare the solid-phase carrier, and a reaction of the solid-phase carrier with a desired amidite compound can be repeated by a solid-phase synthesis method using the above solid-phase carrier, for example, by means of a nucleic acid synthesizer (AKTA Oligopilot 100 plus (produced by GE Healthcare), or the like) to synthesize RNA. Here, "amidite compound" herein refers to a compound containing a structure of amidite, and examples thereof include a nucleoside phosphoramidite in which a hydroxyl group is protected.

The amidite compound to be used in the RNA solid-phase synthesis method is not particularly limited, and examples of the amidite compound to be used may include TBDMS amidite (TBDMS RNA Amidites, product name, Chem-Genes Corporation), ACE amidite, TOM amidite, CEE amidite, CEM amidite, TEM amidite (Reviews by Chakhmakhcheva: Protective Groups in the Chemical Synthesis of Oligoribonucleotides, Russian Journal of Bioorganic Chemistry, 2013, Vol. 39, No. 1, pp. 1-21.), and EMM amidite (as described in WO2013/027843 A1), or the like, in which the protecting group R$^5$ in the following structural formula (2) represents tert-butyldimethylsilyl (TBDMS) group, bis(2-acetoxy)methyl (ACE) group, (triisopropylsilyloxy)methyl (TOM) group, (2-cyanoethoxy)ethyl (CEE) group, (2-cyanoethoxy)methyl (CEM) group, para-tolylsulfonylethoxymethyl (TEM) group, (2-cyanoethoxy) methoxymethyl (EMM) group, or the like.

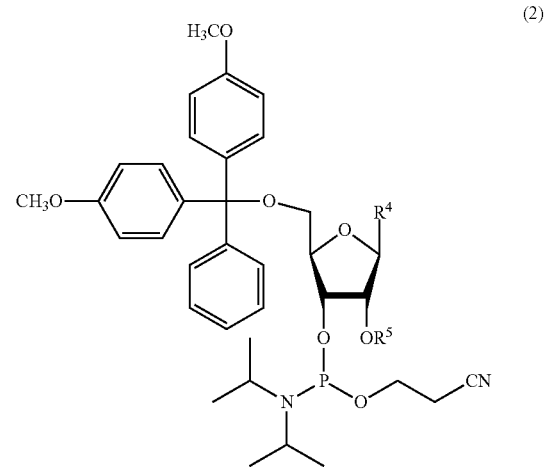

(2)

[wherein, in the formula (2), R$^4$ represents a nucleobase which may be optionally protected, and R$^5$ represents a protecting group.]

As the amidite compound, an amidite having a proline framework represented by the following structural formula (3) (Amidite 2) may also be used (see Example A4 of WO2012/017919 A1). Further, the following amidite represented by each of structural formulae (III-c), (III-d) and (III-e) (see Examples A1 to A3 of WO2013/103146 A1) may also be used to synthesize a nucleic acid.

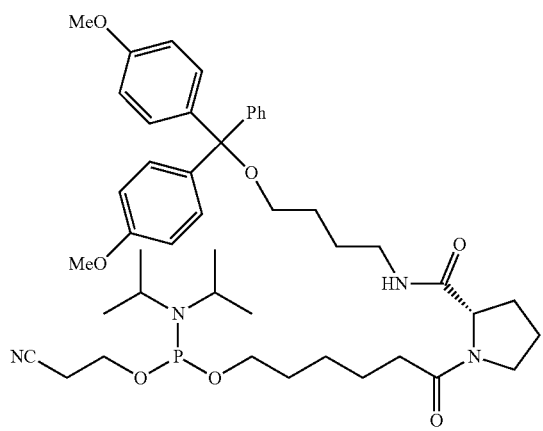

(3)

[wherein, in the formula (3), Me represents a methyl group, and Ph represents a phenyl group.]

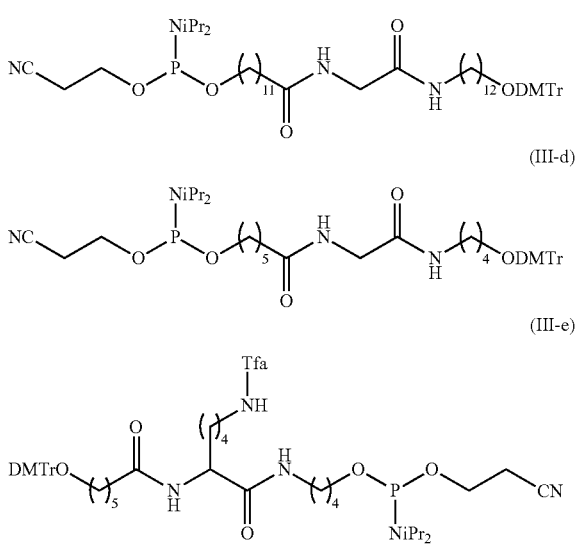

[wherein, iPr represents an isopropyl group, DMTr represents a 4,4'-dimethoxytrityl group, and Tfa represents a trifluoroacetyl group.]

A base which is composed of the nucleotide in the amidite compound is usually a nucleic acid, and typically a naturally-occurring base which is composed of RNA, but a non-naturally-occurring base may be used in some cases.

Examples of such a non-naturally-occurring base include a modified analog of a naturally-occurring base or non-naturally-occurring base.

Examples of the base include, for example, a purine base such as adenine and guanine; a pyrimidine base such as cytosine, uracil and thymine; or the like, which is represented by $R^4$ in the above formula (2). In addition, examples of the base include inosine, thymine, xanthine, hypoxanthine, nebularine, isoguanisine, tubercidine, or the like. Examples of the base include, for example, amino derivatives such as 2-aminoadenine, 2-aminopurine, 2,6-diaminopurine; alkyl derivatives such as 5-methyluracil, 5-methylcytosine, 7-methylguanine, 6-methylpurine, 2-propylpurine; 5-halouracil and 5-halocytosine; 5-propynyluracil and 5-propynylcytosine; 6-azauracil, 6-azacytosine and 6-azathymine; 5-uracil (pseudouracil), 4-thiouracil, 5-(2-aminopropyl)uracil, and 5-aminoallyluracil; 8-substituted purines, for example, 8-halogenated, aminated, thiolated, thioalkylated or hydroxylated purine, or other 8-substituted purine; 5-substituted pyrimidines, for example, 5-trifluoromethylated pyrimidine, or other 5-substituted pyrimidine; 6-azapyrimidine; N-2, N-6 or O-6 substituted purines (including 2-aminopropylade ine); dihydrouracil; 3-deaza-5-azacytosine; 7-deazaadenine; N6-methyladenine, N6,N6-dimethyladenine; 5-amino-allyl-uracil; N3-methyluracil; substituted 1,2,4-triazole; 2-pyridinone; 5-nitroindole; 3-nitropyrrole; 5-methoxyuracil; uracil-5-oxyacetic acid; 5-methoxycarbonylmethyluracil; 2-thiouracil; 5-methyl-2-thiouracil; 5-methoxycarbonylmethyl-2-thiouracil; 5-methylaminomethyl-2-thiouracil; 3-(3-amino-3-carboxypropyl) uracil; 3-methylcytosine; N4-acetylcytosine; 2-thiocytosine; N6-methyladenine; N6-isopentyladenine; 2-methylthio-N6-isopentenyladenine; N-methylguanine; O-alkylated bases, or the like; and two or more thereof. Further, examples of purines and pyrimidines include those disclosed in each of U.S. Pat. No. 3,687,808; "Concise Encyclopedia Of Polymer Science And Engineering", pp. 858-859, edited by Kroschwitz J. I., John Wiley & Sons, 1990; and Englisch et al., Angewandte Chemie, International Edition, 1991, vol. 30, p. 613.

A step of binding a nucleoside containing hydroxyl group, which provides a starting point of a nucleic acid elongation reaction, to the primary amino group of the inorganic porous carrier is described below. A ribonucleoside linker or universal linker which is known for solid-phase nucleic acid synthesis can be used for the reaction in this step. As the ribonucleoside linker and the universal linker, publicly known linkers can be used without particular limitation. When the ribonucleoside linker is used, a ribonucleoside linker corresponding to the base at the 3'end is selected depending on the sequence of RNA to be synthesized.

Examples of the ribonucleoside linker or universal linker include a linker containing a succinyl group as a functional group that can react with the primary amino group (which is referred to as succinyl linker). Further, examples thereof include a linker wherein a hydroxyl group that provides a starting point of the nucleic acid elongation reaction is protected by a protecting group such as dimethoxytrityl (DMTr) group.

Nucleic Acid Elongation Reaction

"A nucleic acid elongation reaction" herein refers to a reaction wherein a nucleic acid strand, in particular an RNA strand, is elongated by sequentially binding nucleotides through a phosphodiester bond. The nucleic acid elongation reaction can be carried out according to the procedure of a usual phosphoramidite method. The nucleic acid elongation reaction may be carried out using an automatic nucleic acid synthesizer or the like that adopts the phosphoramidite method.

In the phosphoramidite method, the nucleic acid elongation reaction is generally carried out by repeating each step of a deprotection step, a condensation step, and an oxidation step.

The deprotection reaction refers to a step of deprotecting a protecting group of a 5'hydroxyl group at an end of the RNA strand supported on the solid-phase carrier. As a general protecting group, a DMTr group is used. The deprotection reaction can be carried out using an acid. Examples of the acid for deprotection include trifluoroacetic acid, dichloroacetic acid, trifluoromethanesulfonic acid, trichloroacetic acid, methanesulfonic acid, hydrochloric acid, acetic acid, p-toluenesulfonic acid, and the like, or two or more thereof.

The condensation step refers to a reaction wherein a nucleoside phosphoramidite is bound to the 5'hydroxyl group at the end of the RNA strand which is deprotected by the deprotection step. As the nucleoside phosphoramidite, a nucleoside phosphoramidite in which the 5'hydroxyl group is protected with a protecting group (for example, DMTr group) is used. The condensation step can be carried out using an activator which activates the above nucleoside phosphoramidite. Examples of the activator include 5-benzylthio-1H-tetrazole (BTT), 1H-tetrazole, 4,5-dicyanoimidazole (DCI), 5-ethyithio-1H-tetrazole (ETT), N-methylbenzimidazolium Lriflate (N-MeBIT), benzimidazolium triflate (BIT), N-phenylimidazolium triflate (N-PhIMT), imidazolium triflate 5-nitrobenzimidazolium triflate (NET), 1-hydroxybenzotriazole (HOBT), 5-(bis-3,5-trifluoromethylphenyl)-1H-tetrazole (Activator-42), and the like, or two or more thereof.

After the condensation step, an unreacted 5'hydroxyl group may be capped as needed. The capping can be carried out using a publicly known capping solution such as acetic anhydride-tetrahydrofuran solution, and phenoxyacetic acid/N-methylimidazole solution.

The oxidation step refers to a step of oxidizing the phosphite ester formed by the condensation step. The oxidation step can be carried out using an oxidizing agent. Examples of the oxidizing agent include iodine, m-chloroperbenzoic acid, tert-butyihydroperoxide, 2-butanoneperoxide, bis (trimethylsilyl) peroxide, 1, 1-dihydroperoxycyclododecane, hydrogen peroxide, and the like, or two or more thereof. The oxidation step may be carried out after the capping operation as described above, or conversely, the capping operation may be carried out after the oxidation step, and accordingly an order of them is not limited thereto.

After the oxidation step, the process returns to the deprotection step, and the above-mentioned steps can be repeated depending on the strand length of RNA strand to be synthesized so as to synthesize RNA having a desired sequence.

After the synthesis of the RNA strand having the desired sequence is completed, the RNA strand is cleaved from the solid-phase carrier by ammonia, amines, or the like, and collected. Examples of the amines include methylamine, ethylamine, isopropylamine, ethylenediamine, diethylamine, triethylamine, and the like, or two or more thereof.

The collected RNA may be purified by a publicly known method, as needed.

RNA synthesis is more difficult than DNA synthesis, and especially in the synthesis of long stranded RNA, the yield and purity could be greatly reduced. However, in the preparation method of the present embodiment, even if the long stranded RNA is synthesized, high yield and purity can be maintained because the above-mentioned solid-phase carrier is used.

Examples of RNA to be synthesized by the preparation method of the present embodiment include RNA of 40-mer or more, or 50-mer or more. An upper limit of the strand length of RNA strand is not particularly limited, but can be set to, for example, 200-mer or less, or 150-mer or less.

Since the RNA obtained by the preparation method of the present embodiment has high purity and good quality, it can be suitably used for a medicament or the like.

The preparation method according to the present embodiment may be a method which comprises steps 1 to 4 as follows:
step 1) a step of reacting the inorganic porous carrier containing the primary amino group with a linker containing a nucleoside having a protected hydroxyl group to introduce the nucleoside having the protected hydroxyl group into the inorganic porous carrier;
step 2) a step of filling a column of a nucleic acid solid-phase synthesizer with the inorganic porous carrier into which the nucleoside is introduced;
step 3) a step of repeating a cycle including deprotection, coupling with an amidite compound, and oxidation multiple times by means of the nucleic acid solid-phase synthesizer; and
step 4) a step of cleaving RNA having the protected hydroxyl group from the inorganic porous carrier after the step 3, and then deprotecting.

A number of cycles in the above step 3) may be set depending on the length of RNA to be synthesized, and may be, for example, 40 times or more, or 50 times or more, or the like. An upper limit of the number of cycles may be set to, for example, 200 times or less, or 150 times or less, or the like.

In another aspect, the present invention also provides a method for preparing RNA, which comprises (a) a step of selecting an inorganic porous carrier containing a primary amino group, wherein an amount of the primary amino group satisfies the following formula (1); and (b) a step of synthesizing RNA by a phosphoramidite method using the inorganic porous carrier.

$$0.7 \leq (I \times R)/S \leq 1.8 \tag{1}$$

wherein,

I: an amount of amino group per unit mass of the inorganic porous carrier (µmol/g), which is measured by a 2-nitrobenzenesulfonic acid adsorption method;

R: a ratio of primary amino group to total amino groups contained in the inorganic porous carrier (amount of the primary amino group/amount of the total amino groups);

S: a specific surface area of the inorganic porous carrier ($m^2$/g), which is measured by a nitrogen adsorption method.

EXAMPLES

Hereinafter, the present invention is described in more detail with reference to Examples, however, the present invention should not be limited to these examples.

Measurement Method

Each of measurement methods used in the following tests is shown below.

Measurement Method 1: Measurement Method of Amino Group Supported on CPG a. 2-Nitrobenzenesulfonic Acid Adsorption Method The inorganic porous carrier 40 to 50 mg was placed in a Pasteur pipette which was sealed with absorbent cotton, and washed by passing a solution 1 mL of 5% by volume N,N-diisopropylethylamine (DIPEA)/tetrahydrofuran (THF) through the inorganic porous carrier. Then, a solution 1 mL of 50 mM 2-nitrobenzenesulfonic acid/THF was passed four times, and then 1 mL of THE was passed four times for washing. Then, using a 10 mL measuring flask as a receiver, a mixed solution, in which a diluted aqueous ammonia solution (a solution obtained by diluting 1 volume of 28% ammonia aqueous solution with 100 volumes of water) and acetonitrile were mixed at a volume ratio of 1:1, was passed through the inorganic porous carrier. The eluted solution received in the measuring flask was diluted with 15% by volume acetonitrile/aqueous solution to provide a 10 mL of solution, which was an analysis sample. The sample was analyzed by high performance liquid chromatography (HPLC) according to the following conditions. Further, the amount of amino group I supported on the inorganic porous carrier was determined based on the calibration line prepared according to the following.

High Performance Liquid Chromatography (HPLC) Analytical Conditions

Column: Scherzo SM-C18 (produced by Imtakat), 4.6 mmφ×150 mm, 3 μm
Mobile phase: Solution A: 10 mM ammonium formate aqueous solution; Solution B: acetonitrile
Gradient condition: A/B =85%/15% (constant)
Flow rate: 1.0 mL/min
Column temperature: 40° C.
Detection wavelength: 210 nm
Injection volume: 10 μL Creation of Calibration Line The 2-nitrobenzenesulfonic acid reagent (2-nitrobenzenesulfonic acid hydrate) used in the above 2-nitrobenzenesulfonic acid adsorption method was subjected to neutralization titration to determine the content of 2-nitrobenzenesulfonic acid in the reagent. Then, three kinds of 2-nitrobenzenesulfonic acid solutions having different concentrations were prepared, and analyzed by HPLC according to the above conditions. The area value of the peak by HPLC was set to a vertical axis, and the concentration of 2-nitrobenzenesulfonic acid was set to a horizontal axis, and the results of HPLC were plotted, and a linear approximation was performed to obtain the calibration line.

Measurement Method 2: CPG Specific Surface Area Measurement Method

A measurement of CPG specific surface area was carried out by the nitrogen adsorption method according to the following procedure.
For a pretreatment of sample, vacuum degassing at 120° C. for 3 hours was carried out by using BELPREP-vacII (produced by MicrotracBell Corp.). To 0.3 g of the pretreated sample, nitrogen gas was adsorbed at a temperature of 77 K while vacuum degassing by using BELSORP-mini (produced by MicrotracBell Corp.), and then desorbed, and the specific surface area S was calculated according to the BET method based on the obtained adsorption isotherm.

Measurement Method 3: Method for Measuring the Supported Amount of Nucleoside

An aqueous 70% perchloric acid solution was diluted with methanol to prepare an aqueous 30% perchloric acid solution. The inorganic porous carrier 40 to 50 mg which supports a nucleoside was placed in a measuring flask, and diluted with the 30% perchloric acid solution to a 20 mL of solution. This solution was further diluted 10-fold with the aqueous 30% perchloric acid solution, and then an absorbance of detached DMTr cation at 498 nm was measured to calculate the supported amount of nucleoside.

Measuring Method 4-a: Method for Measuring the Purity of Oligonucleotide

The purity of the crude oligonucleotide product after solid-phase synthesis was measured by HPLC. The crude product was separated into each component thereof by HPLC (wavelength 260 nm, column DNA Pac™ PA100 4×250 mm), and the purity of the oligonucleotide was calculated based on an area value of a main product in a total area value according to the obtained chromatogram.

Measurement Method 4-b: Method for Measuring the Purity of Oligonucleotide

The purity of the crude oligonucleotide product after solid-phase synthesis was measured by HPLC. The crude product was separated into each component thereof by HPLC (wavelength 260 nm, column ACQUITY UPLC Oigonucleotide BHE C18, 2.1 mm×100 mm), and the purity of the oligonucleotide was calculated based on an area value of a main product in a total area value according to the obtained chromatogram.

Preparation of Inorganic Porous Carrier Containing Primary Amino Group

An amino group modification of CPG was carried out as below to prepare the inorganic porous carriers of Examples to 17 and Comparative Examples 1 to 6. Tables 1 and 2 collectively show the physical properties of CPG (Controlled Pore Glass) used in each of Examples and Comparative Examples, and the amount of amino group of the corresponding inorganic porous carrier containing the primary amino group.

Examples 1 to 9

Amino group-modified CPGs were provided as the inorganic porous carriers of Examples 1 to 9. The physical properties of the CPG used in each of Examples 1 to 9, and the amount of amino group supported on the inorganic porous carrier thereof are shown in Table 1.

Example 10

Amino Group Modification

CPG (6.07 g), which was subjected to dehydration by azeotrope with toluene using a Dean-Stark apparatus in advance, was placed in a 200 mL four-necked flask, and toluene (40.6 mL) was added thereto. Further, [3-(6-aminohexylamino)-propyl]trimethoxysilane (121 μL, 425.8 μmol) was added thereto, and the mixture was heated under reflux at 110° C. for 4 hours. Then, the reaction solution cooled to room temperature was removed by filtration, the residue was washed successively with toluene, methanol and water, and then neutralized with 1N hydrochloric acid. Further, the neutralized solution was removed by filtration, and the residue was washed successively with water and methanol, and dried under reduced pressure to obtain an amino group-modified CPG as a white powdery solid (an inorganic porous carrier containing amino group). The physical properties of the CPG and the amount of amino group thereof are shown in Table 1.

Example 11

Amino Group Modification

The same method as Example 10 except for that CPG (6.36 g), toluene (42.5 mL), and [3-(6-aminohexylamino)-propyl]trimethoxysilane (72.3 µL, 254.4 µmol) were used was carried out to obtain an amino group-modified CPG as a white powdery solid (an inorganic porous carrier containing amino group). The physical properties of the CPG and the amount of amino group thereof are shown in Table 1.

Example 12

Amino Group Modification

CPG (3.00 g) was placed in a 200 mL 4-neck flask, and toluene (23.1 mL) was added thereto. Further, 3-(trimethoxysilyl) propylamine (27.5 µL, 156.5 µmol) was added thereto, and the mixture was heated under reflux at 110° C. for 4 hours. Then, the reaction solution cooled to room temperature was removed by filtration, and the residue was washed successively with toluene, methanol and water, and then neutralized with 1N hydrochloric acid. Further, the neutralized solution was removed by filtration, and the residue was washed successively with water and methanol, and dried under reduced pressure to obtain an amino group-modified CPG as a white powdery solid (an inorganic porous carrier containing amino group). The physical properties of the CPG and the amount of amino group thereof are shown in. Table 1.

Example 13

Amino Group Modification

The same method as Example 10 except for that CPG (6.90 g), toluene (46.2 mL), [3-(6-aminohexylamino)-propyl]trimethoxysilane (58 µL, 204.1 µmol) were used was carried out to obtain an amino group-modified CPG as a white powdery solid (an inorganic porous carrier containing amino group). The physical properties of the CPG and the amount of amino group thereof are shown in Table 2.

Example 14

Amino Group Modification

The same method as Example 10 except for that CPG (6.92 g), toluene (46.3 mL), [3-(6-aminohexylamino)-propyl]trimethoxysilane (58 µL, 204.1 µmol) and trimethoxy (methyl)silane (87.0 µL, 613.1 µmol) were used was carried out to obtain an amino group-modified CPG as a white powdery solid (an inorganic porous carrier containing amino group). The physical properties of the CPG and the amount of amino group thereof are shown in Table 2.

Example 15

Amino Group Modification

The same method as Example 10 except for that CPG (6.82 g), toluene (52.5 mL), and [3-(6-aminohexylamino)-propyl]trimethoxysilane (46 µL, 163.3 µmol) were used was carried out to obtain an amino group-modified CPG as a white powdery solid (an inorganic porous carrier containing amino group). The physical properties of the CPG and the amount of amino group thereof are shown in Table 2.

Example 16

Amino Group Modification

The same method as Example 10 except for that CPG (6.87 g), toluene (45.9 mL), [3-(6-aminohexylamino)-propyl]trimethoxysilane (44 µL, 153.8 µmol) and trimethoxy (methyl)silane (29 µL, 205.1 µmol) were used was carried out to obtain an amino group-modified CPG as a white powdery solid (an inorganic porous carrier containing amino group). The physical properties of the CPG and the amount of amino group thereof are shown in Table 2.

Example 17

Amino Group Modification

The same method as Example 10 except for that CPG (6.95 g), toluene (46.5 mL), and [3-(6-aminohexylamino)-propyl]trimethoxysilane (81.5 µL, 286.8 µmol) were used was carried out to obtain an amino group-modified CPG as a white powdery solid (an inorganic porous carrier containing amino group). The physical properties of the CPG and the amount of amino group thereof are shown in Table 2.

Comparative Examples 1 and 2

As inorganic porous carriers of Comparative Examples 1 and 2, CPGs supporting Lcaa(C9) with an amount of amino group as shown in Table 1 were used.

Comparative Example 3

Amino Group Modification

CPG (6.17 g) having the physical properties as shown in Table 1 was placed in a 200 mL four-necked flask, and toluene (41.1 mL) was added thereto. Further, [3-(6-aminohexylamino)-propyl]trimethoxysilane (238 µL, 837.6 µmol) was added thereto, and the mixture was heated under reflux at 110° C. for 4 hours. Then, the reaction solution cooled to room temperature was removed by filtration, the residue was washed successively with toluene, methanol and water, and then neutralized with 1N hydrochloric acid. Further, the neutralized solution was removed by filtration, and the residue was washed successively with water and methanol, and dried under reduced pressure to obtain an amino group-modified CPG as a white powdery solid (an inorganic porous carrier containing amino group). The physical properties of the CPG and the amount of amino group thereof are shown in Table 1.

Comparative Example 4

Amino Group Modification

CPG (7.00 g) was placed in a 200 mL 4-neck flask, and toluene (53.9 mL) was added thereto. Further, 3-(trimethoxysilyl)propylamine (335.0 µL, 1905.9 µmol) was added thereto, and the mixture was heated under reflux at 110° C. for 4 hours. Then, the reaction solution cooled to room temperature was removed by filtration, and the residue was washed successively with toluene, methanol and water, and neutralized with 1N hydrochloric acid. Further, the neutralized solution was removed by filtration, and the residue was washed successively with water and methanol, and dried under reduced pressure to obtain an amino group-modified CPG as a white powdery solid (an inorganic porous carrier containing amino group). The physical properties of the CPG and the amount of amino group thereof are shown in Table 1.

Comparative Example 5

Amino Group Modification

CPG (5.00 g) having the physical properties as shown in Table 2 was placed in a 200 mL four-necked flask, and toluene (33.5 mL) was added thereto. Further, [3-(6-amino-hexylamino)-propyl]trimethoxysilane (286 µL, 1006.4 µmol) was added thereto, and the mixture was heated under reflux at 110°C. for 4 hours. Then, the reaction solution cooled to room temperature was removed by filtration, and the residue was washed successively with toluene, methanol and water, and neutralized with 1N hydrochloric acid. Further, the neutralized solution was removed by filtration, and the residue was washed successively with water and methanol, and dried under reduced pressure to obtain an amino group-modified CPG as a white powdery solid (an inorganic porous carrier containing amino group). The physical properties of the CPG and the amount of amino group thereof are shown in Table 2.

Comparative Example 6

Amino Group Modification

CPG (5.09 g) having the physical properties as shown in Table 2 was placed in a 200 mL four-necked flask, and toluene (33.5 mL) was added thereto. Further, [3-(6-amino-hexylamino)-propyl]trimethoxysilane (186 µL, 652.8 µmol) was added thereto, and the mixture was heated under reflux at 110° C. for 4 hours. Then, the reaction solution cooled to room temperature was removed by filtration, and the residue was washed successively with toluene, methanol and water, and neutralized with 1N hydrochloric acid. Further, the neutralized solution was removed by filtration, and the residue was washed successively with water and methanol, and dried under reduced pressure to obtain an amino group-modified CPG as a white powdery solid (an inorganic porous carrier containing amino group). The physical properties of the CPG and the amount of amino group thereof are shown in Table 2.

Amount of Amino Group Supported Per Specific Surface Area ((I×R)/S)

Measurement of Supported Amount Of Amino Group I

According to the method of the above measurement method 1, an amount of amino group supported on the inorganic porous carrier of each of Examples 1 to 17 and Comparative Examples 1 to 6 was determined. The results are shown in Tables 1 and 2 as "Amino Group Amount I".

Measurement of Specific Surface Area of CPG

According to the method of the above measurement method 2, a specific surface area of CPG used for the inorganic porous carrier of each of Examples 1 to 17 and Comparative Examples 1 to 6 was determined. The results are shown in Tables 1 and 2 as "Specific Surface Area S".

Calculation of Amount of Primary Amino Group Per Specific Surface Area ((I×R)/S)

An supported amount of amino group per specific surface area ((I×R)/S) according to each of Examples 1 to 17 and Comparative Examples 1 to 6 was calculated on the basis of the above determined supported amount of amino group "I" and the specific surface area of CPG "S". The results are shown in Tables 1 and 2 as "Amount of Primary Amino Group per Specific Surface Area ((I×R)/S)". Here, in Examples 1 to 11 and 13 to 17, and Comparative Examples 1 to 3, 5 and 6, Lcaa(C9) used as a linker for supporting an amino group was used, and a ratio "R" of primary amino group to total amino groups contained in the inorganic porous carrier is 1/2 (i.e. 0.5). Meanwhile, in Example 12 and Comparative Example 4, Aminopropyl used as a linker for supporting an amino group was used, and a ratio "R" of primary amino group to total amino groups contained in the inorganic porous carrier is 1/1 (i.e. 1).

Preparation of Nucleoside Supported on Inorganic Porous Carrier

Inorganic Porous Carrier of Example 1

A rG-succinate 154.9 mg, HBTU (1-[bis(dimethylamino) methylene]-1H-Penzotriazolium 3-Oxide hexafluorophosphate) 63.1 mg, N,N-diisopropylethylamine 39.5 µL and acetonitrile 12 mL were mixed, and about 3.0 g of the inorganic porous carrier of Example 1 which was supported with amino group was added thereto. The resulting was allowed to stand at 25° C. for 20 hours, and then was filtered, and the solid was washed with 100 mL of acetonitrile. To the washed solid, a solution 25 mL of phenoxyacetic acid anhydride 0.35 mol/L (a mixed solvent of tetrahydrofuran/pyridine, volume ratio 8/1) was added. The resulting was allowed to stand for 3 hours, and then was filtered, and the solid was washed with 100 mL of acetonitrile, and then dried to obtain a CPG which was supported with nucleoside as a white powdery solid (an inorganic porous carrier containing nucleoside).

Inorganic Porous Carrier of Example 2

The reaction was carried out according to the same method using the inorganic porous carrier in the above Example 1 except for that rG-succinate 174.1 mg, HBTU 84.0 mg, N,N-diisopropylethylamine 72.3 µL, and acetonitrile 12 mL were mixed, and about 3.0 g of the inorganic porous carrier of Example 2 which was supported with amino group.

The same method as the method used for the inorganic porous carrier of Example 1 except for the above matters was carried out to obtain a CPG which was supported with nucleoside as a white powdery solid (an inorganic porous carrier containing nucleoside).

Inorganic Porous Carrier of Example 3

The reaction was carried out according to the same method using the inorganic porous carrier in the above Example 1 except for that rG-succinate 224.5 mg, HBTU 100.6 mg, N,N-diisopropylethylamine 86.1 µL and acetonitrile 12 mL were mixed, and about 3.0 g of the inorganic porous carrier of Example 3 which was supported with amino group. The same method as the method used for the inorganic porous carrier of Example 1 except for the above matters was carried out to obtain a CPG which was supported with nucleoside as a white powdery solid (an inorganic porous carrier containing nucleoside).

Inorganic Porous Carrier of Example 4

The reaction was carried out according to the same method using the inorganic porous carrier in the above Example 1 except for that rG-succinate 114.3 mg, HBTU 46.7 mg, N,N-diisopropylethylamine 24.0 µL and acetonitrile 12 mL were mixed, and about 3.0 g of the inorganic porous carrier of Example 4 which was supported with amino group. The same method as the method used for the inorganic porous carrier of Example 1 except for the above matters was carried out to obtain a CPG which was supported with nucleoside as a white powdery solid (an inorganic porous carrier containing nucleoside).

Inorganic Porous Carrier of Example 5

The reaction was carried out according to the same method using the inorganic porous carrier in the above
Example 1 except for that rG-succinate 160.0 mg, HBTU 65.7 mg, N,N-diisopropylethylamine 32.9 µL and acetonitrile 12 mL were mixed, and about 3.0 g of the inorganic porous carrier of Example 5 which was supported with amino group. The same method as the method used for the inorganic porous carrier of Example 1 except for the above matters was carried out to obtain a CPG which was supported with nucleoside as a white powdery solid (an inorganic porous carrier containing nucleoside).

Inorganic Porous Carrier of Example 6

The reaction was carried out according to the same method using the inorganic porous carrier in the above Example 1 except for that rG-succinate 193.2 mg, HBTU 93.4 mg, N,N-diisopropylethylamine 80.0 µL and acetonitrile 12 mL were mixed, and about 3.0 g of the inorganic porous carrier of Example 6 which was supported with amino group. The same method as the method used for the inorganic porous carrier of Example 1 except for the above matters was carried out to obtain a CPG which was supported with nucleoside as a white powdery solid (an inorganic porous carrier containing nucleoside).

Inorganic Porous Carrier of Example 7

The reaction was carried out according to the same method using the inorganic porous carrier in the above Example 1 except for that rG-succinate 206.2 mg, HBTU 92.8 mg, N,N-diisopropylethylamine 79.3 µL and acetonitrile 12 mL were mixed, and about. 3.0 g of the inorganic porous carrier of Example 7 which was supported with amino group. The same method as the method used for the inorganic porous carrier of Example 1 except for the above matters was carried out to obtain a CPG which was supported with nucleoside as a white powdery solid (an inorganic porous carrier containing nucleoside).

Inorganic Porous Carrier of Example 8

The reaction was carried out according to the same method using the inorganic porous carrier in the above Example 1 except for that rG-succinate 211.2 mg, HBTU 94.8 mg, N,N-diisopropylethylamine 81.1 µL and acetonitrile 12 mL were mixed, and about 3.0 g of the inorganic porous carrier of Example 8 which was supported with amino group. The same method as the method used for the inorganic porous carrier of Example 1 except for the above matters was carried out to obtain a CPG which was supported with nucleoside as a white powdery solid (an inorganic porous carrier containing nucleoside).

Inorganic Porous Carrier of Example 9

The reaction was carried out according to the same method using the inorganic porous carrier in the above Example 1 except for that rG-succinate 251.9 mg, HBTU 113.2 mg, N,N-diisopropylethylamine 96.7 µL and acetonitrile 12 mL were mixed, and about 3.0 g of the inorganic porous carrier of Example 9 which was supported with amino group. The same method as the method used for the inorganic porous carrier of Example 1 except for the above matters was carried out to obtain a CPG which was supported with nucleoside as a white powdery solid (an inorganic porous carrier containing nucleoside).

Inorganic Porous Carrier of Example 10

The reaction was carried out according to the same method using the inorganic porous carrier in the above
Example 1 except for that rG-succinate 135.4 mg, HBTU 56.0 mg, N,N-diisopropylethylamine 35.0 µL and acetonitrile 12 mL were mixed, and about 2.5 g of the inorganic porous carrier of Example 10 which was supported with amino group. The same method as the method used for the inorganic porous carrier of Example 1 except for the above matters was carried out to obtain a CPG which was supported with nucleoside as a white powdery solid (an inorganic porous carrier containing nucleoside).

Inorganic Porous Carrier of Example 11

The reaction was carried out according to the same method using the inorganic porous carrier in the above Example 1 except for that rG-succinate 161.9 mg, HBTU 68.0 mg, N,N-diisopropylethylamine 45.0 µL and acetonitrile 12 mL were mixed, and about 2.5 g of the inorganic porous carrier of Example 11 which was supported with amino group. The same method as the method used for the inorganic porous carrier of Example 1 except for the above matters was carried out to obtain a CPG which was supported with nucleoside as a white powdery solid (an inorganic porous carrier containing nucleoside).

Inorganic Porous Carrier of Example 12

A rG-succinate 259.4 mg, HBTU 96.8 mg, N,N-diisopropylethylamine 65.0 µL and acetonitrile 15 mL were mixed, and the inorganic porous carrier 2.31 g of Example 12 which was supported with amino group was added thereto. The resulting was allowed to stand at 25° C. for 21 hours, and then was filtered, and the solid was washed with 80 mL of acetonitrile. To the washed solid, a solution 46 mL of phenoxyacetic acid anhydride 0.35 mol/L (a mixed solvent of tetrahydrofuran/pyridine, volume ratio 8/1) was added. The resulting was allowed to stand for 3 hours, and then was filtered, and the solid was washed with 80 mL of acetonitrile, and then dried to obtain a CPG which was supported with nucleoside as a white powdery solid (an inorganic porous carrier containing nucleoside).

Inorganic Porous Carrier of Comparative Example 1

The reaction was carried out according to the same method using the inorganic porous carrier in the above Example 1 except for that rG-succinate 286.0 mg, HBTU 128.1 mg, N,N-diisopropylethylamine 109.4 μL and acetonitrile 12 mL were mixed, and about 3.0 g of the inorganic porous carrier of Comparative Example 1 which was supported with amino group. The same method as the method used for the inorganic porous carrier of Example 1 except for the above matters was carried out to obtain a CPG which was supported with nucleoside as a white powdery solid (an inorganic porous carrier containing nucleoside).

Inorganic Porous Carrier of Comparative Example 2

The reaction was carried out according to the same method using the inorganic porous carrier in the above Example 1 except for that rG-succinate 94.2 mg, HBTU 42.2 mg, N,N-diisopropylethylamine 36.1 μL and acetonitrile 12 mL were mixed, and about 3.0 g of the inorganic porous carrier of Comparative Example 2 which was supported with amino group. The same method as the method used for the inorganic porous carrier of Example 1 except for the above matters was carried out to obtain a CPG which was supported with nucleoside as a white powdery solid (an inorganic porous carrier containing nucleoside).

Inorganic Porous Carrier of Comparative Example 3

The reaction was carried out according to the same method using the inorganic porous carrier in the above Example 1 except for that. rG-succinate 123.3 mg, HBTU 50.2 mg, N,N-diisopropylethylamine 35.0 μL and acetonitrile 12 mL were mixed, and about 2.5 g of the inorganic porous carrier of Comparative Example 3 which was supported with amino group. The same method as the method used for the inorganic porous carrier of Example 1 except for the above matters was carried out to obtain a CPG which was supported with nucleoside as a white powdery solid (an inorganic porous carrier containing nucleoside).

Inorganic Porous Carrier of Comparative Example 4

A rG-succinate 676.7 mg, HBTU 251.2 mg, N, N-diisopropylethylamine 170.0 μL and acetonitrile 15 mL were mixed, and the inorganic porous carrier 3.00 g of Comparative Example 4 which was supported with amino group was added thereto. The resulting was allowed to stand at 25° C. for 18 hours, and then was filtered, and the solid was washed with 100 mL of acetonitrile. To the washed solid, a solution 60 mL of phenoxyacetic acid anhydride 0.35 mol/L (a mixed solvent of tetrahydrofuran/pyridine, volume ratio 8/1) was added. The resulting was allowed to stand for 3 hours, and then was filtered, and the solid was washed with 100 mL of acetonitrile, and then dried to obtain a CPG which was supported with nucleoside as a white powdery solid (an inorganic porous carrier containing nucleoside).

The structure of rG-succinate used in the above methods is shown as follows.

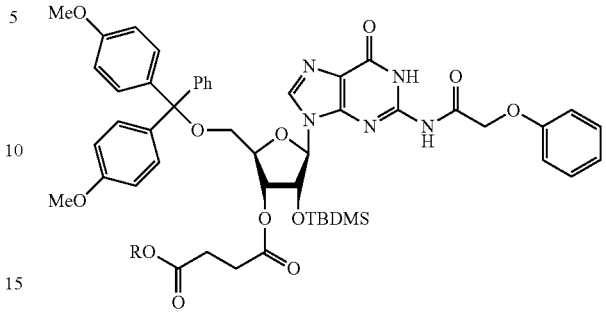

(rG-succinate)
[wherein, R represents a hydrogen atom, a pyridine salt (=pyridine+H), or a triethylamine salt (=triethylamine+H), Me represents a methyl group, Ph represents a phenyl group, and TBDMS represents tert-butyldimethylsilyl group.]

Inorganic Porous Carrier of Example 13

A rU-succinate 93.0 mg, HBTU 47.1 mg, N,N-diisopropylethylamine 31.0 μL and acetonitrile 12 mL were mixed, and 2.50 g of the inorganic porous carrier of Example 13 which was supported with amino group was added thereto. The resulting was allowed to stand at 25°C for 18 hours, and then was filtered, and the solid was washed with 83 mL of acetonitrile. To the washed solid, a solution 13 mL of 10% acetic acid anhydride (a mixed solvent of 80% THF/10% pyridine) and a solution 13 mL of 16% NMI (1-methylimidazole) in 84% THF were added. The resulting was allowed to stand for 1 hour, and then was filtered, and the solid was washed with 83 mL of acetonitrile, and then dried to obtain a CPG which was supported with nucleoside as a white powdery solid (an inorganic porous carrier containing nucleoside).

Inorganic Porous Carrier of Example 14

The reaction was carried out according to the same method using the inorganic porous carrier in the above Example 13 except for that rU-succinate 89.1 mg, HBTU 44.5 mg, N,N-diisopropylethylamine 29.3 μL and acetonitrile 12 mL were mixed, and 2.50 g of the inorganic porous carrier of Example 14 which was supported with amino group. The same method as the method of Example 13 except for the above matters was carried out to obtain a CPG which was supported with nucleoside as a white powdery solid (an inorganic porous carrier containing nucleoside).

Inorganic Porous Carrier of Example 15

The reaction was carried out according to the same method using the inorganic porous carrier in the above Example 13 except for that rU-succinate 133.4 mg, HBTU 66.9 mg, N,N-diisopropylethylamine 39.2 μL and acetonitrile 12 mL were mixed, and 2.50 g of the inorganic porous carrier of Example 15 which was supported with amino group. The same method as the method used for the inorganic porous carrier of Example 13 except for the above matters was carried out to obtain a CPG which was supported with nucleoside as a white powdery solid (an inorganic porous carrier containing nucleoside).

Inorganic Porous Carrier of Example 16

The reaction was carried out according to the same method using the inorganic porous carrier in the above Example 13 except for that rU-succinate 137.8 mg, HBTU 69.2 mg, N,N-diisopropylethylamine 40.0 μL and acetonitrile 12 mL were mixed, and 2.50 g of the inorganic porous carrier of Example 16 which was supported with amino group. The same method as the method used for the inorganic porous carrier of Example 13 except for the above matters was carried out to obtain a CPG which was supported with nucleoside as a white powdery solid (an inorganic porous carrier containing nucleoside).

Inorganic Porous Carrier of Example 17

The reaction was carried out according to the same method using the inorganic porous carrier in the above Example 13 except for that rU-succinate 117.5 mg, HBTU 58.3 mg, N,N-diisopropylethylamine 40.0 μL and acetonitrile 12 mL were mixed, and 2.50 g of the inorganic porous carrier of Example 17 which was supported with amino group. The same method as the method used for the inorganic porous carrier of Example 13 except for the above matters was carried out to obtain a CPG which was supported with nucleoside as a white powdery solid (an inorganic porous carrier containing nucleoside).

Inorganic Porous Carrier of Comparative Example 5

The reaction was carried out according to the same method using the inorganic porous carrier in the above Example 13 except for that rU-succinate 410.0 mg, HBTU 210.0 mg, N,N-diisopropylethylamine 150.0 μL and acetonitrile 12 mL were mixed, and 2.50 g of the inorganic porous carrier of Comparative Example 5 which was supported with amino group. The same method as the method used for the inorganic porous carrier of Example 13 except for the above matters was carried out to obtain a CPG which was supported with nucleoside as a white powdery solid (an inorganic porous carrier containing nucleoside).

Inorganic Porous Carrier of Comparative Example 6

The reaction was carried out according to the same method using the inorganic porous carrier in the above Example 13 except for that rU-succinate 280.0 mg, HBTU 140.0 mg, N,N-diisopropylethylamine 95.0 μL and acetonitrile 12 mL were mixed, and 2.50 g of the inorganic porous carrier of Comparative Example 6 which was supported with amino group. The same method as the method used for the inorganic porous carrier of Example 13 except for the above matters was carried out to obtain a CPG which was supported with nucleoside as a white powdery solid (an inorganic porous carrier containing nucleoside).

The structure of rU-succinate used in the above methods is shown as follows.

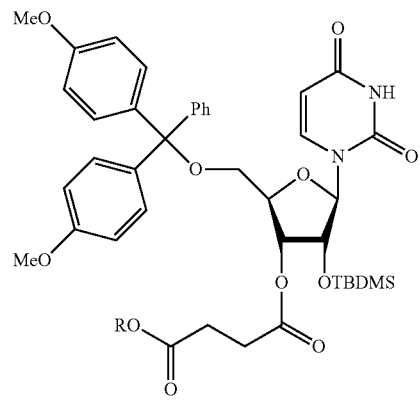

(rU-succinate)

[wherein, R represents a hydrogen atom, a pyridine salt (=pyridine+H), or a triethylamine salt (=triethylamine+H), Me represents a methyl group, Ph represents a phenyl group, and TBDMS represents tert-butyldimethylsilyl group.]

Measurement of Supported Amount of Nucleoside

According to the method of the above measurement method 3, an amount of nucleoside group supported on the inorganic porous carrier of each of Examples 1 to 12 and Comparative Examples 1 to 4 was determined. The results are shown in Table 1 as "Supported Amount of Tr".

Solid-Phase Synthesis of Long-Stranded Oligonucleotide

Inorganic Porous Carriers of Examples 1 to 12 and Comparative Examples 1 to 4

```
Sequence (A):
                                     (SEQ ID NOs: 1 and 2)
5'-AGCAGAGUACACACAGCAUAUACC-P-GGUAUAUGCUGUGUGUACUC UGCUUC-P-G-3' 53-mer.

(SEQ ID NO: 1)
AGCAGAGUACACACAGCAUAUACC
and (SEQ ID NO: 2)
GGUAUGAUGCUGUGUGUACUCUGCUUC.
```

In the above sequence (A), "P" represents a partial structure separated with wavy lines in the following chemical formula.

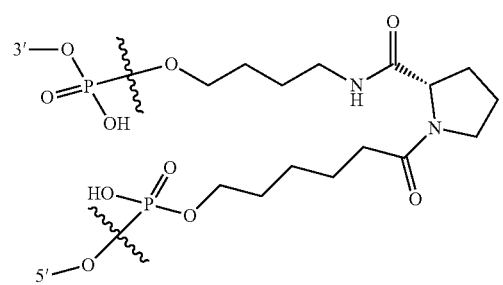

The inorganic porous carrier of any one of Examples 1 to 12 and Comparative Examples 1 to 4 which was supported with nucleoside, as prepared in the above methods was used as the solid-phase carrier, and AKTA Oligopilot 100plus (produced by GE Healthcare) was used as a nucleic acid synthesizer, and the oligonucleotide consisting of the above sequence (A) was synthesized from the 3'side to the 5'side according to the phosphoramidite solid-phase synthesis method. In the synthesis, the uridine EMM amidite described in Example 2 of US2012/0035246 A1, the cytidine EMM amidite described in Example 3 of the same, the adenosine EMM amidite described in Example 4 of the same, the guanosine EMM amidite described in Example 5 of the same, and the compound (3) described in WO2017/188042 A1 were used. A solution of highly pure trichloroacetic acid in toluene was used as a deblocking solution, 5-benzylmercapto-1H-tetrazole was used as a condensing agent, an iodine solution was used as an oxidizing agent, and a phenoxyacetic acid solution and an N-methylimidazole solution were used as a capping solution.

Inorganic Porous Carriers of Examples 13 to 17 and Comparative Examples 5 to 6

Sequence (B):
(SEQ ID NO: 3)
5'-AUAACUCAAUUUGUAAAAAAGUUUUAGAGCUAGAAAUAGCAAGUUAA

AAUAAGGCUAGUCCGUUAUCAACCUUGAAAAAGUGGCACCGAGUCGGUGC

UUUUUUU-3' 103-mer.

(Jinek M, Chylinski K, Fonfara I, Hauer M, Doudna J A, Charpentier E. A programmable dual-RNA-guided DNA endonuclease in adaptive bacterial immunity. Science. 2012 Aug 17; 337(6096):816-21.)

The inorganic porous carrier of any one of Examples 13 to 17 and Comparative Examples 5 to 6 which was supported with nucleoside, as prepared in the above methods was used as the solid-phase carrier, and AKTA Oligopilot 100plus (produced by GE Healthcare) was used as a nucleic acid synthesizer, and the oligonucleotide consisting of the above sequence (B) was synthesized from the 3'side to the 5'side according to the phosphoramidite solid-phase synthesis method. In the synthesis, the uridine EMM amidite described in Example 2 of US2012/0035246 A1, the cytidine EMM amidite described in Example 3 of the same, the adenosine EMM amidite described in Example 4 of the same, and the guanosine EMM amidite described in Example 5 of the same were used. A solution of highly pure trichloroacetic acid in toluene was used as a deblocking solution, 5-benzylmercapto-1H-tetrazole was used as a condensing agent, an iodine solution was used as an oxidizing agent, and a phenoxyacetic acid solution and an N-methylimidazole solution were used as a capping solution.

Release of Oligonucleotide From Solid-Phase Carrier and Deprotection Thereof

Inorganic porous carriers of Examples 1 to 17 and Comparative Examples 1 to 6

After the completion of the above solid-phase synthesis using any one of the inorganic porous carriers of Examples 1 to 17 and Comparative Examples 1 to 6, the inorganic porous carrier was taken such that an amount of supported nucleoside corresponded to 8.1 µmol. An aqueous ammonia solution and subsequent tetra-n-butylammonium fluoride (TBAF) were acted thereto in the presence of nitromethane to release the oligonucleotide from the solid-phase carrier and to conduct a deprotection thereof, and thereby a crude product was obtained.

Measurement of Oligonucleotide Yield

The $OD_{260}$ of the above crude product was measured. "OD260" refers to an absorbance at UV 260 nm per 10 mm optical path length with a solution 1 mL (pH =7.5). Since it is generally known that 1 OD-40 µg in RNA, the yield was calculated based on the above measured value of $OD_{260}$. Further, the yield per unit volume of the inorganic porous carrier was calculated. In each of Examples 1 to 12 and Comparative Examples 1 to 4, the relative yield with respect to the yield of Example 2 was determined, and the result is shown in Table 1 as "Relative Yield per Unit Volume". In each of Examples 13 to 17 and Comparative Examples 5 to 6, the relative yield with respect to the yield of Example 13 was determined, and the result is shown in Table 2 as "Relative Yield per Unit Volume".

Measurement of Purity

Inorganic Porous Carriers of Examples 1 to 12 and Comparative Examples 1 to 4

The purity of the oligonucleotide synthesized with the inorganic porous carrier of each of Examples 1 to 12 and Comparative Examples 1 to 4 was measured according to the method of the above measurement method 4-a. The results are shown in Table 1 as "Purity".

Inorganic porous carriers of Examples 13 to 17 and Comparative Examples 5 to 6

The purity of the oligonucleotide synthesized with the inorganic porous carrier of each of Examples 13 to 17 and Comparative Examples 5 to 6 was measured according to the method of the above measurement method 4-b. The results are shown in Table 2 as "Purity".

TABLE 1

|  | Pore Size (nm) | Amino Group Type | Amino Group Amount I (µmol/g) | Specific Surface Area S (m²/g) | Amount of Primary Amino Group per Specific Surface Area (I × R)/S (µmol/m²) | Supported Amount of Tr (µmol/g) | Strand Length of RNA synthesized (mer) | Relative Yield per Unit Volume | Purity*[1] (%) |
|---|---|---|---|---|---|---|---|---|---|
| Example 1 | 111 | Lcaa(C9) | 89.9 | 30.5 | 1.47 | 39.6 | 53 | 1.02 | 70 |
| Example 2 | 111 | Lcaa(C9) | 89.9 | 30.5 | 1.47 | 41.9 | 53 | 1.00 | 70 |

TABLE 1-continued

|  | Pore Size (nm) | Amino Group Type | Amino Group Amount I (μmol/g) | Specific Surface Area S (m²/g) | Amount of Primary Amino Group per Specific Surface Area (I × R)/S (μmol/m²) | Supported Amount of Tr (μmol/g) | Strand Length of RNA synthesized (mer) | Relative Yield per Unit Volume | Purity*1 (%) |
|---|---|---|---|---|---|---|---|---|---|
| Example 3 | 113 | Lcaa(C9) | 91.7 | 30.7 | 1.49 | 42.9 | 53 | 1.00 | 70 |
| Example 4 | 113 | Lcaa(C9) | 101.9 | 30.7 | 1.66 | 37.1 | 53 | 0.99 | 69 |
| Example 5 | 113 | Lcaa(C9) | 101.9 | 30.7 | 1.66 | 39.3 | 53 | 1.00 | 73 |
| Example 6 | 113 | Lcaa(C9) | 101.9 | 30.7 | 1.66 | 44.8 | 53 | 1.00 | 70 |
| Example 7 | 113 | Lcaa(C9) | 105.9 | 30.7 | 1.72 | 44.9 | 53 | 1.01 | 70 |
| Example 8 | 113 | Lcaa(C9) | 102.7 | 30.7 | 1.67 | 44.8 | 53 | 1.00 | 69 |
| Example 9 | 107 | Lcaa(C9) | 112 | 34.5 | 1.62 | 49.1 | 53 | 1.02 | 69 |
| Example 10 | 104 | Lcaa(C9) | 97.6 | 36.0 | 1.36 | 40.4 | 53 | 1.01 | 71 |
| Example 11 | 111 | Lcaa(C9) | 63.3 | 43.7 | 0.72 | 29.6 | 53 | 0.84 | 71 |
| Example 12 | 107 | Aminopropyl | 50 | 34.5 | 1.45 | 35.4 | 53 | 0.94 | 71 |
| Comparative Example 1 | 107 | Lcaa(C9) | 158.5 | 34.5 | 2.3 | 55.4 | 53 | 0.91 | 44 |
| Comparative Example 2 | 107 | Lcaa(C9) | 158.5 | 34.5 | 2.3 | 34.4 | 53 | 0.82 | 42 |
| Comparative Example 3 | 104 | Lcaa(C9) | 154.9 | 36.0 | 2.15 | 45.7 | 53 | 0.93 | 54 |
| Comparative Example 4 | 107 | Aminopropyl | 156.8 | 34.5 | 4.54 | 50.6 | 53 | 0.84 | 54 |

*1Purity was determined according to the measurement method 4-a.

TABLE 2

|  | Pore Size (nm) | Amino Group Type | Amino Group Amount I (μmol/g) | Specific Surface Area S (m²/g) | Amount of Primary Amino Group per Specific Surface Area (I × R)/S (μmol/m²) | Strand Length of RNA synthesized (mer) | Relative Yield per Unit Volume | Purity*2 (%) |
|---|---|---|---|---|---|---|---|---|
| Example 13 | 124 | Lcaa(C9) | 48.3 | 31.4 | 0.77 | 103 | 1.00 | 63 |
| Example 14 | 124 | Lcaa(C9) | 44.6 | 31.4 | 0.71 | 103 | 0.92 | 61 |
| Example 15 | 178 | Lcaa(C9) | 36.1 | 23.7 | 0.76 | 103 | 0.69 | 63 |
| Example 16 | 178 | Lcaa(C9) | 40.9 | 23.7 | 0.86 | 103 | 0.71 | 61 |
| Example 17 | 124 | Lcaa(C9) | 57.4 | 31.4 | 0.91 | 103 | 1.03 | 62 |
| Comparative Example 5 | 124 | Lcaa(C9) | 203.1 | 31.4 | 3.23 | 103 | 0.94 | 10 |
| Comparative Example 6 | 178 | Lcaa(C9) | 140.3 | 23.7 | 2.96 | 103 | 0.70 | 19 |

*2Purity was determined according to the measurement method 4-b.

As shown in Tables 1 and 2, in the inorganic porous carrier used in each of Examples 1 to 17, the amount of primary amino group supported per specific surface area of the inorganic porous carrier ((I×R)/S) was within a range of 0.7 to 1.8 μmol/m². On the other hand, in the inorganic porous carrier used in each of Comparative Examples 1 to 6, it was shown that (I×R)/S>1.8 μmol/m², which was out of the above range. In each of Examples 1 to 12, the purity of the oligonucleic acid was significantly improved as compared with Comparative Examples 1 to 4. Also, in each of Examples 13 to 17, the purity of the oligonucleic acid was significantly improved as compared with Comparative Examples 5 and 6.

INDUSTRIAL APPLICABILITY

The present invention provides a method for preparing RNA which can improve the purity even in medium-stranded to long-stranded RNA synthesis. The RNA obtained by the preparation method according to the embodiment of the present invention is useful as a raw material for pharmaceutical products.

Sequence Listing Free Text

SEQ ID NOs: 1 to 3 in the sequence listing represent the base sequences of oligonucleotides prepared according to the preparation method of the present invention.
Sequence Listing

The invention claimed is:

1. A method for preparing RNA, the method comprising:
conducting a phosphoramidite solid-phase synthesis using an inorganic porous carrier comprising a primary amino group,
wherein the inorganic porous carrier is obtainable by reacting an inorganic porous substance with a silane coupling agent comprising a primary amino group or a protected primary amino group, wherein the inorganic porous substance in the inorganic porous carrier is porous glass, wherein the porous glass is Controlled Pore Glass,
wherein an amount of the primary amino group in the inorganic porous carrier satisfies the following formula (1):

$$0.7 \leq (I \times R)/S \leq 1.8 \tag{1}$$

wherein
I is an amount of amino group per a unit mass of the inorganic porous carrier in μmol/g measured by a 2-nitrobenzenesulfonic acid adsorption method;
R is a ratio of the primary amino group to total amino groups in the inorganic porous carrier, amount of the primary amino group/amount of the total amino groups;
S is a specific surface area of the inorganic porous carrier in m$^2$/g measured by a nitrogen adsorption method.

2. The method for preparing RNA according to claim 1, wherein the amount of the primary amino group in the inorganic porous carrier satisfies the following formula (1'):

$$1.3 \leq (I \times R)/S \leq 1.8 \tag{1'}$$

3. The method according to claim 1, wherein the inorganic porous carrier has a pore size, which is a mode diameter, of from 90 to 120 nm.

4. The method according to claim 1, wherein the inorganic porous carrier has a pore size, which is a mode diameter, of from 120 to 200 nm.

5. The method according to claim 1, comprising:
reacting the inorganic porous carrier comprising the primary amino group with a linker comprising a nucleoside having a protected hydroxyl group, thereby introducing the nucleoside having the protected hydroxyl group into the inorganic porous carrier;
filling a column of a nucleic acid solid-phase synthesizer with the inorganic porous carrier into which the nucleoside has been introduced;
repeating a cycle comprising deprotecting, coupling with an amidite compound, and oxidating multiple times using the nucleic acid solid-phase synthesizer;
cleaving RNA having the protected hydroxyl group from the inorganic porous carrier, and deprotecting a protecting group of the protected hydroxyl group.

6. The method according to claim 5, wherein the linker is a succinyl linker.

7. The method according to claim 5, wherein the cycle is repeated for at least 40 times.

8. The method according to claim 1, wherein the inorganic porous substance has an average particle size of from 1 μm to 1000 μm measured by scattering type laser diffraction.

9. The method according to claim 1, wherein a specific surface area of the inorganic porous substrate is from 10 m$^2$/g to 100 m$^2$/g.

10. The method according to claim 5, wherein the cycle is repeated from 40 to 200 times.

* * * * *